(12) United States Patent
de Munck et al.

(10) Patent No.: US 9,156,018 B2
(45) Date of Patent: Oct. 13, 2015

(54) VAPORISATION IN OXIDATION TO PHTHALIC ANHYDRIDE

(71) Applicant: ExxonMobil Chemical Patents Inc., Baytown, TX (US)

(72) Inventors: Nicolaas A. de Munck, Barendrecht (NL); Aad G. Oskam, Rozenburg (NL); Evert C. Klein, Dorst (NL)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 14/159,951

(22) Filed: Jan. 21, 2014

(65) Prior Publication Data

US 2014/0134066 A1    May 15, 2014

Related U.S. Application Data

(62) Division of application No. 12/673,420, filed as application No. PCT/EP2008/061934 on Sep. 9, 2008, now Pat. No. 8,703,974.

(51) Int. Cl.
*B01J 8/06* (2006.01)
*B01J 4/00* (2006.01)
*C07C 51/265* (2006.01)

(52) U.S. Cl.
CPC *B01J 8/067* (2013.01); *B01J 4/002* (2013.01); *B01J 8/065* (2013.01); *C07C 51/265* (2013.01); *B01J 2208/00176* (2013.01); *B01J 2208/00849* (2013.01); *B01J 2208/00902* (2013.01)

(58) Field of Classification Search
CPC ............. B01J 8/065; B01J 2208/00902; B01J 2219/0027; B01J 2219/00265
See application file for complete search history.

(56) References Cited

U.S. PATENT DOCUMENTS

| | | | |
|---|---|---|---|
| 2,310,907 A | 2/1943 | McMillan | |
| 3,681,399 A * | 8/1972 | Barth | 549/250 |
| 4,119,645 A | 10/1978 | Auroy et al. | |
| 4,259,981 A * | 4/1981 | Busse | 137/375 |
| 4,435,581 A | 3/1984 | Miserlis | |
| 4,528,006 A * | 7/1985 | Vitovec et al. | 55/360 |
| 4,647,436 A | 3/1987 | Herbort et al. | |
| 4,936,351 A * | 6/1990 | Wells et al. | 138/89 |
| 5,214,157 A | 5/1993 | Healy et al. | |
| 6,984,289 B2 | 1/2006 | Domes et al. | |
| 2003/0013931 A1 | 1/2003 | Block et al. | |

FOREIGN PATENT DOCUMENTS

| | | |
|---|---|---|
| DE | 202005012 725 | 12/2005 |
| DE | 102004052827 | 5/2006 |
| EP | 1 273 919 | 1/2003 |

(Continued)

OTHER PUBLICATIONS

Machine Translation of DE 20 2005 012 725.*

*Primary Examiner* — Lessanework Seifu
(74) *Attorney, Agent, or Firm* — Leandro Arechederra, III; Luke A. Parsons

(57) ABSTRACT

In the production of phthalic anhydride by the oxidation of ortho-xylene with air, the ortho-xylene loading is increased without increasing the likelihood of explosion by insulating the system to avoid cold spots to keep the ortho-xylene at a temperature above its dew point; in addition the system may be electrically interconnected and grounded to reduce the risk of spark initiated explosions or deflagrations.

8 Claims, 4 Drawing Sheets

(56) References Cited

FOREIGN PATENT DOCUMENTS

| GB | 1239803 | 7/1971 |
| GB | 1550036 | 8/1979 |
| WO | 01/47622 | 7/2001 |
| WO | 2009/402045 | 4/2009 |

* cited by examiner

VAPORISATION IN OXIDATION TO PHTHALIC ANHYDRIDE

CROSS REFERENCE TO RELATED APPLICATIONS

This application is a Divisional Application of U.S. Ser. No. 12/673,420 filed Jun. 7, 2011, now allowed, which is a 371 National Stage Application of International Application No. PCT/EP2008/061934, Sep. 9, 2008 which claims the benefit of Great Britain Application No. 0718995.4, filed Sep. 28, 2007, the disclosures of which are herein incorporated by reference in their entireties.

FIELD OF THE INVENTION

The present invention relates to a process and apparatus for the production of phthalic anhydride, and in particular to the configuration of systems for the generation and handling of mixtures of ortho-xylene and an oxygen-containing gas, particularly air, as the reactor feedstock for the production of phthalic anhydride, which mixtures contain more than 44 grams of ortho-xylene per normal cubic meter of air and are thus flammable and explosive. The invention further relates to the production of phthalate ester and hydrogenated phthalate ester derivatives.

BACKGROUND OF THE INVENTION

Phthalic anhydride is an important intermediate chemical in the chemical industry. One important use is in the production of phthalates such as di-isononyl or di-isodecyl phthalates, which are used as plasticisers, typically for polyvinyl chloride. Phthalic anhydride has been produced on an industrial scale for many years and has generally been produced by the vapour phase oxidation of ortho-xylene with an oxygen-containing gas, such as air, by passing a mixture of ortho-xylene and the oxygen-containing gas over an oxidation catalyst.

A typical plant for the production of phthalic anhydride comprises a raw material delivery section, a raw material mixing section in which a hot mixture of the oxygen-containing gas and ortho-xylene vapour is prepared and a mixture delivery section for feeding to a reaction system comprising the reactor which typically consists of reactor tubes containing catalyst. The components of these sections are known as the process equipment. The reaction is exothermic and the temperature of the reactor tubes is controlled by a temperature control fluid, such as molten salt, flowing around the tubes.

After the reaction, the crude phthalic anhydride that has been produced passes to a cooling stage where it is cooled, generally by a gas cooler, passed to optionally a liquid condenser and finally to a switch condenser. Finally, the condensed phthalic anhydride is subjected to a purification or finishing step.

The efficiency of a phthalic anhydride plant is measured in terms of the number of grams of ortho-xylene that can be processed for each cubic meter of air that is fed to the raw material section (known as the loading). The greater the amount of ortho-xylene, the greater is the efficiency of the facility. Considerable attempts have been made over the years to increase the loading, and loadings above 80 gram/$Nm^3$ of ortho-xylene in air have been reported.

One difficulty in the manufacture of phthalic anhydride is that, at the temperatures required for the reaction of air and ortho-xylene the mixture becomes flammable and explosive at a loading above 44 gram of ortho-xylene per normal cubic meter of air. Accordingly, great care must be taken to avoid or reduce the likelihood of explosions. When an explosion occurs and the flame velocity exceeds the velocity of sound, this supersonic explosion is called a detonation. Otherwise, at subsonic flame velocities, it is called a deflagration. By the provision of an adequate number of escape ducts, such as chimneys, sealed off by rupture discs, at critical locations, the occurrence of a detonation is avoided, while the burning gas from a deflagration is relieved to a safe location. One or more rupture discs are conveniently located on the ortho-xylene vaporizer, at the reactor inlet and outlet, and on downstream equipment and the sections of the piping operating within the flammability limits. These rupture discs can be of any suitable design, although reverse buckling or bending rod type are preferred. One of the areas in a phthalic anhydride facility that is prone to a deflagration is the raw material mixing section, where the ortho-xylene and the air are mixed. One of the reasons for a deflagration to occur is if there is incomplete vaporisation or condensation in the vapour/air mixture at the time when it reaches the oxidation catalyst. Other reasons can be poor mixing of the heated ortho-xylene and the heated air, inhomogeneity in the composition of the mixture, discharges from the build-up of static electricity, or the decomposition of peroxides formed from feed impurities like cumene or styrene. The present invention is concerned with reducing or minimising the likelihood of a deflagration of an explosion occurring.

In a typical commercial process the generation of a feed gas mixture has to date been performed as follows. Process air is sucked in from the surroundings through a filter by means of a blower, and compressed to a pressure level which allows the conveyance of the air stream through the phthalic anhydride plant. This process air stream is heated in a heat exchanger disposed downstream of the blower. Parallel thereto, liquid ortho-xylene from a storage tank is brought to a preliminary pressure by means of a pump and passed through a basket type filter and a preheater before it is fed to an evaporator, vaporizer drum or spray drum. In the evaporator, the preheated ortho-xylene is injected in liquid form into the heated air stream parallel to the air flow, by means of a nozzle system. The fine ortho-xylene droplets completely evaporate in the air stream, and a further smoothening of the radial concentration and temperature profiles in the gas stream is achieved by means of a homogenisation stage (a homogenizer section comprising e.g. a static mixer). This feed gas subsequently enters the reactor, typically a tubular reactor comprising of tubes filled with catalyst to provide a catalyst bed, where a partial oxidation of ortho-xylene with the oxygen takes place to form phthalic anhydride.

This process for the generation of feed gas has successfully been used, but with the successive introduction of higher ortho-xylene loads in the air stream (above 80 g ortho-xylene per $Nm^3$ air) the process has shown potential weaknesses with regard to the explosion safety of the raw material section of the plant. The lower explosion limit of a gaseous mixture of ortho-xylene and air is about 44 g of ortho-xylene per $Nm^3$ of air. It has been found that the minimum energy required for igniting the mixture is greatly decreased with increasing ortho-xylene load, and therefore the desire to increase the ortho-xylene loading increases the possibility of an explosion. However, to a great extent, the economics of the overall phthalic anhydride production process depends upon increasing the load of ortho-xylene per $Nm^3$ air. It is therefore of basic importance that plants with a loading in the range of 80 g ortho-xylene/$Nm^3$ air to 120 g ortho-xylene/$Nm^3$ air must be operated safely.

U.S. Pat. No. 6,984,289 B2 relates to a process for the production of phthalic anhydride by the oxidation of ortho-xylene with air and with a loading of 80 g to 100 g of ortho-xylene per $Nm^3$ of air. This higher loading is said to be made possible by complete evaporation followed by superheating of the ortho-xylene prior to admixture with air. U.S. Pat. No. 4,435,581 discloses a process wherein naphthalene is first completely evaporated before bringing the vapours in contact with the air stream in a reactor containing a fluidised bed of oxidation catalyst. DE 20 2005 012 725 U1 provides a system in which ortho-xylene is sprayed through nozzles into an air stream in which the flow cross-section of the air feed tube is reduced downstream of the spray nozzles, so that vapour velocity and turbulence are increased, thereby improving the mixing of the reaction components, and in this way the risk of explosion is reduced. DE 20 2005 012 725 U1 also provides a cone-shaped perforated screen at either side of the spray nozzles to divert the pressure wave from an explosion occurring in the evaporation section towards the rupture discs, thereby protecting the equipment upstream and downstream from these screens from damage by a shock wave. These screens assist also in homogenising the flow of air and the flow of the air/ortho-xylene mixture.

U.S. Pat. No. 4,119,645 also relates to a process for the production of phthalic anhydride by the oxidation of a mixture of ortho-xylene with air, but is silent about how the mixture is produced and passed to the oxidation reactor. U.S. Pat. No. 4,119,645 is not concerned with the homogeneity of the mixture or how to preserve it until it reaches the catalyst. Patents GB 1550036 and GB 1239803 also relate to processes for the production of phthalic anhydride by the oxidation of a mixture of ortho-xylene with air. The processes operate at loadings of ortho-xylene in air that are below or barely above the lower explosion limit and much lower than current industrial practice. These processes are therefore much less sensitive to an inhomogeneity in the ortho-xylene/air mixture. GB 1550036 and GB 1239803 are silent about the production of the ortho-xylene/air mixture and the passing thereof to the oxidation reactor. These documents are not concerned with the homogeneity of the mixture or how to preserve it until it reaches the catalyst.

United States patent application US 2003/0013931 A1 relates to a process and apparatus for producing a homogeneous mixture of ortho-xylene vapour in air, as feed to an oxidation reactor for the production of phthalic anhydride. US 2003/0013931 A1 is concerned with rapid vaporisation of the ortho-xylene into the air stream, and employs special spray nozzles to that effect. The spraying is performed in a chamber bounded by side walls heated to a temperature above the boiling point of ortho-xylene, such that droplets of ortho-xylene which impinge on the tube wall are vaporised immediately and do not deposit as a liquid film. US 2003/0013931 A1 is not concerned with avoiding condensation on surfaces in contact with the ortho-xylene/air mixture as it passes to the catalyst in the reactor. It is silent about the surfaces between the end of the heatable double-walled tube and the top tubesheet of the reactor. US 2003/0013931 A1 is also silent about any rupture disks that may for safety reasons be provided on the inlet head of the oxidation reactor, in the raw material mixing section or in the section delivering the mixture to the catalytic reactor. These rupture disks are safety devices and in a heatable double-wall version would not be readily able to perform their critical function. US 2003/0013931 A1 is not aware of the problems of possible condensation of ortho-xylene on the internal surfaces of these rupture disks or the flanges and piping connecting thereto. It is therefore not concerned with the temperature of internal surfaces of rupture disks or other equipment elements up to the inlet of the catalyst bed in the oxidation reactor.

It is important that a homogenous mixture of ortho-xylene and air is formed for feeding to the reactor and this may be accomplished by enhancing the rate of ortho-xylene vaporisation. As is described in our co-filed UK application reference GB 0718994.7, we have found that this may be accomplished by employing a particular nozzle system, and a particular set of conditions within the nozzle, to spray the ortho-xylene into the hot air, and in particular GB 0718994.7 is concerned with a system for mixing ortho-xylene with an oxygen-containing gas, which system comprises an ortho-xylene evaporator or vaporiser vessel fed with a stream of oxygen-containing gas and provided with at least one lance projecting into the stream of oxygen-containing gas, which lance is provided with at least one metal spray nozzle adapted to inject droplets of liquid ortho-xylene into the stream of oxygen-containing gas concurrently with the direction of flow of the stream of oxygen-containing gas, in which the metal at the surface of the spray nozzle, that in use is in contact with the liquid ortho-xylene, has a hardness expressed as a Vickers hardness number according to ASTM E92-82 of at least 200, preferably at least 250 and more preferably at least 600. The spray nozzle is preferably made of hardened steel, more particularly surface hardened austenitic stainless steel. The desired surface hardness is preferably obtained by nitriding the nozzle surface, more preferably by cold nitriding such as by Kolsterising®.

In addition, the applicants co-filed application reference GB 0718994.7 describes a particular sealing system to prevent the leakage of liquid ortho-xylene at undesired locations from the spray nozzle system. This spray nozzle system, including the sealing system preferably comprising an annealed copper seal ring, is particular useful when used in combination with a specially designed oxygen-containing gas feed system and a particular design of oxygen-containing gas and ortho-xylene mixing system.

In operation, ortho-xylene is preheated to about 140° C. under elevated pressure, flow metered with mass flow meters, and forced into a spray nozzle configuration for injection into the heated oxygen-containing gas, which is typically air. The hot liquid ortho-xylene is thus sprayed as a fine mist into the hot air upon which the ortho-xylene is vaporised. The present invention is concerned with maintaining the ortho-xylene in the vapour phase. Furthermore, it is important that the ortho-xylene does not coalesce or condense and form liquid deposits within the raw material section of the plant, to reduce the risk of explosion when liquid deposits are formed. When ortho-xylene is allowed to condense on internal surfaces in the equipment up to the inlet tubesheet of the tubular reactor, relatively large droplets may come loose from the surface and be entrained by the mixture of ortho-xylene vapour and the oxygen-containing gas. Entrained larger droplets may not be totally vaporised by the time they reach the oxidation catalyst bed, and cause a local excessive reaction, increasing the risk for a runaway reaction and possible catalyst damage, and for an explosion. When such entrained larger droplets become totally vaporised but only just before they reach the catalyst bed, they may still be causing smaller volumes in the vapour/gas mixture in which the concentration of ortho-xylene is higher than average. Such an inhomogeneity may also cause a local excessive reaction when reaching the catalyst, and trigger an explosion. In order to reduce the explosion risk it is therefore not only important to rapidly vaporise the ortho-xylene that is sprayed into the oxygen-containing gas, it is also important to avoid condensation of ortho-xylene from the mixture on internal surfaces of the equipment from the production of the vapour/gas mixture up to the inlet tubesheet of the reactor.

SUMMARY OF THE INVENTION

According to the present invention, a process is provided for the manufacture of phthalic anhydride by the catalytic oxidation of ortho-xylene, comprising producing in a raw material preparation step, by spraying a heated ortho-xylene liquid feed into a preheated oxygen-containing gas feed, a mixture of ortho-xylene vapour and the oxygen-containing gas, and passing the mixture to a reaction section comprising a fixed bed tubular catalytic reactor for performing the reaction step in which phthalic anhydride is formed, characterised in that the mixture and the surfaces of the process equipment that are in contact with the mixture are maintained at a temperature above the dew point of ortho-xylene in the mixture, during the production of the mixture and the passage of the mixture to the catalytic reactor.

The manufacture of phthalic anhydride according to the present invention requires the production of an as homogenous as possible mixture of oxygen-containing gas and ortho-xylene, which is to be maintained at a temperature above the dew point temperature of ortho-xylene in the mixture, and it is this mixture that is fed to the oxidation reactor. The dew point is the temperature that is reached when the first liquid forms within a vapour mixture that is being cooled, and for the mixture of ortho-xylene and oxygen-containing gas depends on the prevailing concentration of ortho-xylene in the mixture, and the pressure to which the mixture is subjected. Dew point as used herein is defined in Perry's Chemical Engineers' Handbook $5^{th}$ Edition Section 13 page 17. By maintaining the surfaces that are in contact with the mixture up to the inlet tubesheet of the tubular reactor at a temperature above the dew point of ortho-xylene in the mixture, condensation of ortho-xylene on those surfaces is avoided, and the formation and entrainment of larger liquid droplets with the mixture as it is passed to the reactor is avoided. The existence of cold spots inside the critical equipment is thus avoided, so that ortho-xylene is not condensed and the risk for local excessive reaction on the catalyst, runaway reactions, catalyst damage, and possibly also explosions is reduced.

DETAILED DESCRIPTION

The raw material preparation section typically comprises a raw material delivery section for introducing the oxygen-containing gas, which is usually air, and a separate raw material delivery section for introducing ortho-xylene liquid. Preferably one, more preferably both of the raw material delivery sections comprise a preheater for preheating the raw material prior to the production of the mixture. Further in the raw material preparation section, in the raw material mixing section, the ortho-xylene is introduced, typically still as a liquid, into the oxygen-containing gas, and the mixture is subsequently passed through homogenisers and mixers in the mixture delivery section to the reaction section. At least one, and preferably several rupture discs are usually provided at appropriate locations to minimise the effect of any deflagration or explosion that may occur inside the process equipment. Observation windows and measuring points may also be provided. All these features of the plant or process equipment can provide cold spots, where ortho-xylene may condense and which thus increase the risk of an explosion or deflagration to occur. The present invention therefore provides for thermal insulation of at least some of the external surfaces of the process equipment and the component parts of the raw material section to maintain the mixture and the surfaces of the process equipment that are in contact with the mixture above the dew point of ortho-xylene in the mixture and thus prevent or reduce the formation of cold spots and thus reduce the tendency for explosions or deflagrations to occur.

We prefer that, in the oxygen-containing gas supply or delivery section, at least one, but preferably all of the external surfaces of preferably all the piping and equipment having a content above ambient temperature is fully insulated, more preferably also including the flanges between piping and connecting the piping with the equipment. More preferably insulation is also provided to the oxygen-containing gas blower discharge and continues until the location where the oxygen-containing gas enters the vaporizer. Also here, we prefer the thermal insulation to be as complete and continuous as possible, e.g. including the flanges.

We also prefer that, in the liquid ortho-xylene delivery section, at least one of the external surfaces of the process equipment through which the ortho-xylene liquid feed passes, is provided with thermal insulation.

We also prefer that the insulation starts at the ortho-xylene preheater of the ortho-xylene feed delivery section, which typically is a steam preheater, and continues to the spray nozzle assemblies. We further prefer that the vaporizer, the mixing device, the mixture delivery section and/or the reactor top hood are, more preferably all and most preferably all fully, insulated, including the vessel flanges and equipment nozzles.

As an alternative to thermal insulation, but preferably in combination therewith, heat may be provided to at least one of the external surfaces or walls of the equipment that is in contact with the mixture and/or the mixture components, particularly the process equipment for the production of the mixture and for passing the mixture to the reactor. This heat may be provided by many possible means, but typically is provided by heat tracing, in the form of electrical tracing or tracing by steam or another heated fluid, or by jacketing, typically steam jacketing.

With heat tracing, a heating source, such as an electrical resistance or a heating tube is provided at the external surface or walls of the process pipe or equipment. The heating tube is preferably a metal tube, typically copper, which is preferred because it is easy to adapt to the shape of the object it is applied to, or stainless steel. The heating tube may contain a heat transfer fluid, such as a hot oil, but preferably contains steam, which provides heat by condensing, upon which the condensate may or may not be recovered. Steam heating is preferred for tracing or jacketing in a phthalic anhydride facility, because of the ample availability of steam generated by the process heat. Electrical tracing may be easier to bring in place, but may be subject to failure in case of power failures.

Heat jacketing, typically steam jacketing, is achieved by surrounding the pipe or equipment with a larger diameter pipe, or by providing an extra envelope around the equipment, or at least parts of it, whereby the heat transfer fluid or steam flows between the larger and the smaller pipe, or through the envelope. An alternative is to connect half diameter pipe onto the external wall of certain equipment items, such as by welding, to form piping with the cross section of about a half circle. The heat transfer fluid is then typically passed through the half diameter or half circle piping.

Preferably the exterior of the vaporizer and the mixing device have half-pipe steam tracing lines which minimize the heat loss from this equipment.

When heat is provided to the outer surface and/or walls of the equipment, it is preferred to have also thermal insulation provided, to preserve the energy that is provided to the heating system.

Very often, thermal insulation and/or the heat providing systems discussed above are provided to the more accessible external surfaces, such as those of pipes and vessels. The flanges between piping sections and which connect piping to equipment, and the equipment nozzles connecting vessels and other equipment items to piping, are typically not insulated and/or traced or jacketed, because the more irregular shapes of their external surfaces make these provisions more difficult. Another reason for not insulating and/or heating the flanges that connect process equipment is the risk that with increased thermal expansion, such as of the bolts, the flange connection may lose its tightness and a leak of process fluid to the outside may develop. The risk of such leaking increases when the flange connection is thermally insulated, and the presence of a leak becomes more difficult to observe. We now have found that, in the critical sections of the phthalic anhydride plant, it is strongly preferred to also have at least one but preferably more than one, most preferably all, equipment nozzles provided with thermal insulation and/or with external heating provisions. This has been found to reduce the occurrence of cold spots, and to be a significant contributor to reducing the occurrence of deflagrations. We found that only providing insulation and/or heat in the conventional way, thereby not covering flanges and/or equipment nozzles, leads to undesirable cold spots in the equipment in contact with the vapour/gas mixture, and to more frequent deflagrations.

We have also found that under heavy rain, rain water may seep into the thermal insulation and reach the hot surface of the equipment. Upon evaporation, this may cause a local cold spot to occur in contact with the vapour/gas mixture. If the evaporation is violent, it may also damage the thermal insulation, which by losing its integrity may increase the risk of further water ingress and hence of cold spot occurrence. We therefore prefer to minimise the ingress of water, hail or snow into the thermal insulation by appropriate measures, such as appropriate sealing of the insulation outer surfaces, especially those directed upwards.

The one or more rupture discs mounted on the process equipment for performing the reaction step and/or the raw material preparation step, and/or for passing the mixture from the raw material preparation step to the reaction step, preferably also have heating provisions as described before, preferably via tracing and more preferably steam tracing, more particularly along the equipment nozzle connecting the vessel with the rupture disc assembly. The tracing is preferably thermally insulated towards the environment, to conserve energy. The equipment nozzle towards a rupture disc, and the flange carrying the rupture disc, are typically of a relatively large size, and these provisions therefore have a more important contribution to the desired effect.

A further cause of explosion or deflagration is that the ortho-xylene, as vapour but particularly as liquid, has the tendency to accumulate static electrical charge when experiencing turbulent flow or shear such as by passing through restrictions, such as filters, pumps, nozzles, flow meters, control valves and spray nozzles, due to its very low conductivity, which is typically about 0.1 picoSiemens per meter for the liquid phase. The Siemens or Mho is the reciprocal of the Ohm. Such a low electrical conductivity implies that ortho-xylene, and especially in its liquid form, has a high resistance for electrostatic charge relaxation. It is therefore preferred to retain the liquid ortho-xylene in the process equipment prior to the production of the mixture for a residence time that is sufficient for static electric charge relaxation. The appropriate residence time can be achieved by appropriate equipment design, such as selecting equipment types that provide larger process fluid holdups, and during operation by e.g. controlling the flow of the ortho-xylene from the pump to the spray nozzles.

The residence time that is particularly important, is the time the liquid ortho-xylene takes for flowing from the location where it may still have picked up electrostatic charge, such as when passing the feed pump, a filter, a flow meter and/or a control valve, up to the inlet of the preheater, and up to the location where the liquid ortho-xylene is sprayed into the oxygen-containing gas, such as in the spray nozzle providing the mixing of the liquid and the gas.

We prefer that the residence time provided for static charge relaxation is at least 60, more preferably at least 75 and most preferably at least 85 seconds.

Even more preferably, we provide such a minimum residence time already in the preheater only, most preferably already in the preheater tubes only. Larger residence times require even bigger equipment, and therefore we prefer the residence time to be at most 100, preferably at most 95 seconds.

In this section of the equipment, we prefer to select equipment items and designs that provide larger process fluid holdups and/or items that minimise or avoid flow turbulence of, and/or shear on, the process fluid. It is preferred to avoid high shear equipment in particular or more generally any equipment that is capable of generating static charge, such as a filter, a flow meter or a control valve, in between the preheating and prior to the production of the mixture, such as up to the spraying by the spray nozzle or nozzles.

In a preferred embodiment the ortho-xylene steam preheater is a shell and tube heat exchanger, with the steam on the shell side and the ortho-xylene on the tube side. Illustrative design conditions are 14.5 barg pressure and 185° C. for the steam side, and 22 barg pressure and 185° C. for the ortho-xylene side. In such a system, the ortho-xylene goes through a multi-tubular heat exchanger, preferably a TEMA Type C exchanger, for example an 18 pass bundle with an outside tube diameter of about 60 mm with a wall thickness of 2 to 3 mm, and we prefer this because of the low liquid flow velocities through exchanger tubes having such or similar dimensions. For a total tube length of about 98 meters in the heat exchanger, a holdup volume of 225 liters will provide a residence time of 85 seconds at 100 g ortho-xylene/Nm$^3$ air loading and 4 Nm$^3$/hr/tube air rate, for a reactor having 21000 tubes. Measurements for low conductivity or accumulator fluids, such as ortho-xylene, have shown that at least 20 seconds relaxation time is sufficient to disseminate more than 63% of an accumulated static electricity charge. Accordingly, the calculated 85 seconds is considered a sufficient holdup for charge relaxation before entering the spray nozzle to reduce the likelihood of the accumulation of an extra static electricity charge on the ortho-xylene droplets to cause explosion or deflagration. With such residence time, a contribution to the explosion risk by static charge accumulation in the liquid ortho-xylene feed system is essentially eliminated.

In a further aspect, the present invention provides a gaseous mixture of ortho-xylene and air containing more than 44 grams of ortho-xylene per Nm$^3$ air at a temperature above 135° C. in which the ortho-xylene is supplied from a preheater and the mixture is passed to an oxidation reactor in which the residence time of the ortho-xylene in the preheater is between 60 and 100 seconds preferably between 75 and 95 seconds.

It is also preferred to provide adequate electrical grounding to earth, either directly or indirectly, of metal parts of preferably all piping, instrumentation and process equipment in those areas that are in contact with ortho-xylene liquid and/or vapour, with the oxygen-containing gas and with the mixture of ortho-xylene vapour and oxygen-containing gas. This grounding preferably starts downstream of the fluid driving means, such as at the outlet of the liquid pumps and/or the gas blowers or compressors.

It is even more preferred, as an alternate but preferably in combination with electrical grounding, to minimize or to eliminate potential differences between connecting flange sets of this equipment, piping and instrumentation by electrical interconnections, such as by providing at least one metal wire cable strongly attached and electrically connected to both of the flanges of at least one connecting flange set, preferably of all connecting flange sets. For such a connection, a metal plate may be welded to the flange, the metal wire cable may be connected to a metal clip or clamp, and the clip or clamp may be bolted to the metal plate to allow for minimum resistance in the electrical connection between the metal cable and the flange. We also found that the cable should preferably be as straight and short as possible with minimal loops. In order to provide a minimum of slack for in case the distance between the cable connection points increases, a U-shaped cable may be most preferred. It is most preferred to have these connections on every part of the ortho-xylene vaporiser or evaporator vessel, as the available hold up volume is limited to allow for sufficient charge dissipation after the ortho-xylene mist has left the spray nozzles, such as to minimise charge separation in the ortho-xylene mist and between the pieces of equipment in contact therewith. A further preference is not to have a thermowell in the vaporiser and homogenizer system where ortho-xylene mist is present because the thermowell can act as an antenna prone for building up a static charge.

We prefer that, in the delivery section for the oxygen-containing gas, every flange between the gas preheater and the vaporizer is connected with its counter-flange by a U-shaped connecting cable of minimum length. The gas preheater is preferably double grounded to earth and the bottom basket of the vaporizer is preferably also independently grounded. Any main block valve in this system preferably has a separate grounding cable.

We also prefer that, in the ortho-xylene feed delivery section, every flange starting from the basket filter inlet to the spray nozzle assemblies is connected with its counter-flange by a U-shaped connecting electrical cable of minimum length. The filters are preferably individually grounded, the ortho-xylene preheater is preferably double grounded on the shell side, and single grounded on the tube side. We also prefer that the emergency block valves near the vaporizer are single grounded independently.

In addition, we prefer that each of the equipment nozzles on the evaporator vessel, through which the spray nozzle assemblies are mounted, is grounded to earth. The same applies to the vaporizer body itself, the top cover with its rupture disc and the rupture disc vent stack.

In our preferred process and apparatus, the connecting flanges between the vaporizer, the static mixer and the reactor are connected to each other by a U-shaped cable and in addition also connected to earth. In addition, we prefer that the reactor top hood flange is connected with a U-shaped cable to the reactor body flange and then also connected to earth. We also prefer that the main reactor body is double grounded. The vent stacks of the reactor rupture discs are preferably also grounded to earth. All reactor instrument connections may also be connected with U-shaped cables across the connecting flanges, and in addition grounded to earth.

Grounding cables may be connected to earth rails which allow for the connection to grounding cables running to common systems. For instance the grounding of the reactor top hood, the mixing device and the vaporizer can all run to the same grounding rail. In this manner the potential difference between the various systems is further minimised as compared with individual direct earthing. In order to improve electrical charge dissipation, electrically conductive construction materials such as metal are preferred above non-conductive materials, such as many polymers.

It is not easy to correlate between gap distance and voltage required for a spark to occur between two electrically charged objects, because it is impacted by the conductivity of the medium between them, and therefore by the composition of this medium. Certain trial and error steps may be required to determine the minimum acceptable gaps for avoiding sparks however, and as a guideline the breakdown strength of air—for a spark to occur—between two sharp edges is about 28,000 volts per inch. Accordingly, a 3 mm gap between two metal pieces in the reactor inlet system would result in 3304 volts maximum allowable voltage potential difference, assuming the mixture of ortho-xylene vapour and oxygen-containing gas behaves like air. Typically 3 mm is the thickness of a gasket between two metal equipment pieces such as with the inlet sieve basket of the evaporator, which is mounted in between two flanges. Similarly the bottom of the outlet sieve basket of the evaporator has this kind of distance to the wall of the evaporator. For the sieve basket, the 3304 volts maximum potential difference represents a stored energy of 0.578 millijoules (mJ), and which energy is released in the spark when one occurs. This is well above the literature value found for the minimum ignition energy of ortho-xylene at these temperatures, which is 0.301 mJ at 125° C. and 0.26 mJ at 150° C. Even the voltage difference of 2203 volts over a 2 mm gap provides sufficient energy to ignite the mixture at a temperature above 150° C. This indicates the importance of providing effective grounding and effective electrical interconnections, particularly for parts of the equipment that are in close proximity to each other.

The present invention further provides an apparatus for the production of phthalic anhydride which comprises a reaction section comprising a fixed bed tubular catalytic reactor, and a raw material preparation section comprising (i) separate raw material delivery sections for a liquid and for a gaseous raw material,
(ii) a raw material mixing section comprising a system for spraying the liquid raw material into the gaseous raw material to form a mixture of vaporised liquid and gas, and
(iii) a mixture delivery section for delivering the mixture of vaporised liquid and gas to the fixed bed catalytic reactor,
(iv) at least one rupture disk on the raw material preparation section and/or on the reaction section wherein the raw material delivery sections each comprise a raw material heater, and wherein the external surfaces of the equipment nozzles, which are provided for connecting individual elements of the process equipment in the raw material preparation section and/or in the reaction section up to the inlet tubesheet of the tubular reactor, and which are in contact with the mixture of vaporised liquid and gas, are thermally insulated.

The apparatus of the invention may also contain any single one, or two or more, or even all the features described herein in relation to the process of the present invention. In particular are meant the following features:

at least one rupture disk, on the fixed bed catalytic reactor and/or the raw material preparation section and/or on the reaction section, wherein an insulating blanket may preferably be provided on the external surface of the rupture disc, a relief stack on the rupture disc, having a foam cap, means for providing heat to external surfaces or walls of equipment in the raw material delivery sections, in the raw material mixing section, in the mixture delivery section, and/or in the reaction section, such means preferably being thermally insulated, means for direct or indirect electrical grounding of metal parts of piping, instrumentation and process equipment, in particular these in contact with the liquid and/or vaporised liquid raw material and/or the oxygen-containing gas and/or the mixture of vaporised liquid and gas, at least one metal cable electrically connecting the two flanges of at least one connecting flange set for connecting equipment components and/or piping and/or instrumentation that in use are in contact with the liquid and/or vaporised liquid raw material and/or the oxygen-containing gas and/or the mixture of vaporised liquid and gas, at least one spray nozzle system comprising at least one lance, which lance comprises at least one spray nozzle for spraying the liquid raw material into the gaseous raw material to form the mixture of vaporised liquid and gas in the raw material mixing section, and a metal seal between the spray nozzle and the lance of the spray nozzle system, preferably made of half soft copper, such as O61 annealed copper according to ASTM B111, because of its softness.

The present invention is particularly useful in combination with the use of the spray nozzle systems for ortho-xylene described in our co-filed application reference GB 0718994.7, wherein preferably at least one lance projects into the raw material mixing section, said lance comprising at least one spray nozzle for spraying the liquid raw material into the gaseous raw material to form the mixture of vaporised liquid and gas in the raw material mixing section, and with the preferred embodiment of that application in which the seal between the nozzles and the lance is provided by a metal seal. The use of a metal seal between the typically metal spray nozzle and the typically metal lance provides a system with good electrical conductivity in which the development of an electrostatic charge is reduced and the risk of explosion is accordingly reduced. Examples of suitable metals from which the seal may be made include copper and aluminium. O61 annealed copper, according to ASTM B111, is the preferred material. We also prefer to provide a conical surface on the spray nozzle where it contacts the copper seal, such that it is self-centring and improves the contacting of the spray nozzle with the metal seal. Even more preferred is to have a conical surface on the metal seal itself, which preferably matches the conical surface of the spray nozzle, if this is present.

Although the invention is workable with only one lance carrying only one spray nozzle, we prefer a plurality of lances and/or preferably a plurality of spray nozzles to be present, thereby forming a spray nozzle system. The invention includes that the features of the invention are present in at least one of the elements of these pluralities, but preferably in most and more preferably in all of the elements.

In a further embodiment, the ortho-xylene is supplied to the lances from the preheater from a single source, through a single line which feeds a supply ring linked to the nozzles around the perimeter or circumference of the vaporiser, depending on whether or not the vaporiser has a circular cross-section at the nozzle system location. In this way, the pressure at which the ortho-xylene is fed to the spray nozzles can be maintained substantially constant, and be substantially the same to all nozzles if more than one are present, leading to the production of a similar mixture of oxygen-containing gas and ortho-xylene by each nozzle.

In a further embodiment, the ortho-xylene is supplied to the spray nozzles from the preheater at a temperature below the flash point of ortho-xylene at the pressure inside the vaporiser Keeping the ortho-xylene below this temperature assures that the ortho-xylene may stay in the liquid phase inside the nozzle. The supply temperature is typically in the range of 120° C. to 160° C. The temperature is preferably only slightly below the flash point and a temperature in the range 135° C. or 137° C. to 142° C., especially 139 or 140° C., is particularly preferred. Use of this temperature enables the liquid ortho-xylene to be swirled together with oxygen-containing gas inside the nozzles, drawing in oxygen-containing gas by the created venturi effect, and is vaporised as it is sprayed out from the spray nozzle in the selected spray pattern, which is typically a spray cone, as provided by the design of the spray nozzle. In addition, because the oxygen-containing gas outside the lance(s) is typically hotter than the liquid ortho-xylene on the inside, heat may be transferred to the ortho-xylene by conduction through the lance walls, and this temperature control range allows for the ortho-xylene to pick up heat before it is sprayed without causing undesirable levels of cavitation in the spray nozzle. We have found that the use of these conditions reduces erosion by cavitation of the spray nozzles, improves the homogeneity of the oxygen-containing gas/ortho-xylene mixture and shortens the time required to reach complete vaporisation. The selected spray cone of the spray nozzle can also reduce the interference between the spray patterns generated by adjacent spray nozzles, which further reduces the likelihood of coalescence and condensation of the ortho-xylene. Furthermore, the spray cone can be selected to prevent direct injection of ortho-xylene onto any metal components which could provide cold spots and a location for condensation and/or coalescence.

Preferably the direction of the spray nozzle centre axis is parallel to the direction of the oxygen-containing gas flow. However, to avoid coalescence of the ortho-xylene droplets, especially when a plurality of spray nozzles is employed, a spray nozzle can be located and/or directed at an angle thereto.

In a preferred design, the evaporator vessel is of substantially circular cross section perpendicular to the direction of the gas flow, and a plurality of lances are provided around the circumference of the evaporator vessel extending across the cross section of the vessel. In yet a further preference, eight lances may be projected into the evaporator vessel, from the circumference of the vessel. Preferably with a plurality of lances, these are positioned equidistant from each other around the perimeter of the vessel.

In a further preference, each lance consists of two limbs of different length, thus extending a different distance across the cross section of the vessel.

Each lance is typically provided with a plurality of spray nozzles, at least one of which may be inclined at an angle of from 0° to 45° to the direction of flow of the stream of oxygen-containing gas, and preferably alternate spray nozzles are inclined relative to each other.

The number of spray nozzles that may be employed depends upon the capacity of the phthalic anhydride facility and the diameter of the vaporiser or evaporator unit.

It is preferred that, when the spray nozzles face sideways, they are inclined at different sides of the longitudinal axis of the lance(s), forming an alternating pattern, thereby avoiding that the spray from one spray nozzle interrupts the spray pattern from an adjacent spray nozzle.

In a further preferred embodiment of a two-limb lance, the larger limb of the lance is provided with ten spray nozzles and the shorter limb is provided with six spray nozzles.

In another further preference the spray nozzle closest to the wall of the vessel is positioned at least 130 mm from the wall of the vessel to avoid the spray cone from the nozzle hitting the vessel wall. It has been found that if spray nozzles are positioned at a distance of less than 100 mm distance from the wall the ortho-xylene spray cone can touch the vessel wall, and can be brought below its dew point and wet spots can occur on the vessel wall increasing the risk of explosion or deflagration.

The lance carrying the spray nozzle(s) is typically hollow for the delivery of the liquid ortho-xylene to the spray nozzle(s) and the end of (each limb of) the lance(s) is preferably capped so that ortho-xylene cannot flow out of the end of the lance or limb.

The design of the spray nozzle itself is also important and we prefer to use a nozzle having a 60-70° spray cone. A vaporising spray nozzle supplied by Schlick-Dusen hollow-cone type 121V with a 1.3 mm bore diameter is particularly useful.

The nozzles are preferably made of hardened stainless steel to minimise wear and corrosion in order to maintain the desired spray cone over extended plant runs. Preferably austenitic stainless steel is used for making the nozzles because of the better corrosion resistance.

As described in co-filed application reference GB 0718994.7, spray nozzles can be damaged by dirt and particles and by any surface treatment, and the resulting damage, in particular of the relatively softer austenitic stainless steel, can be reduced by manufacturing the spray nozzles from hardened stainless steel. This is conveniently achieved by surface hardening of the steel spray nozzle.

The surface hardening may conveniently be accomplished by nitriding, preferably by cold temperature nitriding to maintain dimensional stability, and more preferably by Kolsterising®.

Slight surface defects in the spray nozzle cause cavitation and erosion and we have found that the two major causes of damage are particles and superheated ortho-xylene. The particles may come from ortho-xylene feed (rust, sand, glass or mineral wool or fibre from tank floating roof seal that erodes) and hence it is important that, as well as being preheated, the feed be filtered. It was found that a 20 micron, basket type filter did not keep all particles out and it is therefore preferred to use, optionally in addition, a 10 micron size cartridge filter more preferably a 5 micron size most preferably a 1 micron size cartridge filter downstream of the pump and the optional basket filter.

It is also important to prevent fouling of the spray nozzle with unwanted material which can come from the upstream equipment and valves, and we prefer to use metal, particularly copper seals to avoid the problem when using Teflon seals, since the Teflon can be softened by the hot ortho-xylene so that Teflon fibres are formed which can plug the spray nozzles. We also have observed that when applying polymer tapes such as polytetrafluorethylene like Teflon these tapes can get damaged by the mechanical forces required for mounting the spray nozzle into the lance. Fragments of damaged tape frequently end up at the interior of the spray nozzle.

It is preferred that the liquid ortho-xylene is fed to the spray nozzles from the ortho-xylene preheater through a common source to the spray nozzles, so that the ortho-xylene is injected under substantially equal pressure from all the nozzles. In this way each nozzle can produce a similar mist of ortho-xylene within the hot oxygen-containing gas stream and the mist can have a substantially uniform ortho-xylene droplet size. In a preferred embodiment ortho-xylene is sprayed through a nozzle system to yield a droplet mass-distribution of from 5 to 15%, typically 10%, of particles that have a diameter not larger than 40 micron, preferably not larger than 35 or not larger than 30 micron, more preferably not larger than 25 or even not larger than 20 micron, from 30 to 70%, typically 50% of particles that have a larger diameter but not larger than 75 micron, preferably not larger than 65 micron, more preferably not larger than 55 or even not larger than 50 micron, from 20 to 40%, typically 30%, of particles having a yet larger diameter but not larger than 110 micron, preferably not larger than 95 micron, more preferably not larger than 75 micron, and the balance from 0 to 15%, typically 10%, of particles having a even yet larger diameter but preferably not larger than 200 micron. We have found that this may be accomplished if the ortho-xylene is sprayed with a differential pressure of at least 5 bar, preferably at least 7 bar, more preferably at least 9 bar and most preferably at least 10 bar, especially 12 bar, through a spraying nozzle having a bore diameter of at most 3 mm, preferably at most 2.5 mm, more preferably at most 2 or even 1.5 mm, and most preferably at most 1.3 mm.

In a further preferred embodiment, the liquid ortho-xylene is fed from a common source. As one alternative of such embodiment, a ring system may be provided for the feed of liquid ortho-xylene to the lances that carry the nozzles. Care should be taken to maintain the ring system and the spray nozzle system at the desired temperature, which may be accomplished by highly effective insulation of the external surface of the piping and other metal parts that compose the ring system and the spray nozzle system, as well as of the piping through which the preheated oxygen-containing gas flow is guided. In addition heat may be provided to these surfaces, which may be provided by steam tracing and/or steam jacketing.

It is also important that there are no leaks of hot liquid into the heated gas stream at undesired locations, such as where the nozzles are attached to the lance. We therefore prefer to have an effective seal between spray nozzles and the lances which carry the spray nozzles and we have found that a metal gasket, particularly a heat treated copper gasket, positioned where the spray nozzle connects with the lances provides an effective seal.

The oxygen-containing gas which is mixed with the preheated ortho-xylene is usually air and is typically ambient air, which is filtered to remove dust, and particularly sea salt because that may poison the oxidation catalyst. The gas is typically preheated, preferably to 180-210° C., usually in two stages. Higher temperatures are required for higher ortho-xylene loadings to ensure a high mixture temperature. At the higher ortho-xylene loadings, of at least 80 grams per Nm3, it is our preference to operate with a reactor inlet temperature of 168-172° C., after passing the homogenizer section, to ensure the completeness of the vaporisation and to reduce the risk of condensation. Preferably before the mixing, the hot gas passes through turbulence reducers ("quieting" vanes). Its flow rate is preferably measured, e.g. by means of a venturi device, so that it may be accurately controlled, such as at about 4 Nm$^3$/h/tube relative to the number of reactor tubes, which is our preferred flow rate.

We have found that providing an additional step for reducing the turbulence in the hot gas before the flow measurement makes it much easier to have an accurate and representative measurement of the gas velocity, e.g. by means of a simple and low pressure drop device as a venturi device, and thus of the gas flow. This may be done by a first set of "quieting" or "straightening" vanes upstream of the flow measurement, and which can be of any suitable type or form to obtain the turbulence reducing effect. We prefer, because of the simplicity of design and construction, to fill the typically large diameter pipe duct for the hot gas, such as e.g. a 48 inch or 122 cm nominal diameter pipe, over a length of at least 1.5 or 2 meter or about 1-2 pipe diameters, as much as possible with preferably thin-walled pipes of a significantly smaller diameter, such as 3 inch (about 8 cm) or 4 inch (about 10 cm) pipes, and preferably using a combination of different diameters to obtain a better filling of the large pipe duct. The better the large diameter pipe duct is filled, the lesser gas can bypass along the perimeter of the vanes and the better the overall quieting effect. Many construction materials can be selected for fabricating these straightening vanes, but we prefer steel, typically carbon steel, because the steel pipes can be welded to each other and the total system can then obtain sufficient structural integrity. We have found that any welding, soldering, brazing or glue applying operation to connect such vanes to each other and/or to the larger pipe duct needs to be performed carefully and with sufficient aftercare and cleaning, because we have found that debris from the connecting operation, such as slag from welding, which may remain in the assembly upon commissioning, can be carried with the gas downstream and disturb operations integrity of the downstream evaporator, the homogeniser and/or even at the reactor inlet. When welding is used, we prefer to use longitudinal welds rather than spot welding because of this reason.

The ortho-xylene is preferentially also filtered, preferably to 1 micron, advantageously preheated in the preheater to 135-145° C., with a residence time of up to 100 seconds preferably between 60 and 90 seconds, and sprayed into the hot gas through the spray nozzle system as a fine mist cloud, so that the ortho-xylene vaporises in the hot gas. As mentioned previously, it is our preference to limit the ortho-xylene preheat temperature to avoid ortho-xylene superheating and flash vaporisation, because this can lead to cavitation inside the spray nozzle, leading to nozzle damage.

When the oxygen-containing gas is air, the ortho-xylene concentration in air is typically between 32 and 120 gram/$Nm^3$ and the reactor may be started for example with a loading of 32 gram/$Nm^3$ and the loading may be gradually increased further to a concentration range of 80-120 grams/$Nm^3$, preferably 90-105 gram/$Nm^3$. The process of the invention is particularly suitable for processing mixtures containing from 44 to 120, preferably from 75 to 120, more preferably from 80 or 85 to 110 grams of ortho-xylene per $Nm^3$ of air.

The mixture of ortho-xylene vapour and oxygen-containing gas passes to the reactor inlet through a homogenizer comprising a perforated screen and a static mixer. The perforated screen helps to deflect shock waves and protect the downstream equipment from shock waves originating in the vaporiser. It is preferred that the static mixer comprises two stages in one of which the mixture passes both from top to bottom and from bottom to top in the vertical plane within the mixer and in the other section it passes from side to side in the horizontal plane within the mixer. It is further preferred that the side to side section is the second section through which the mixture passes. In a further preference at least one but preferably all metal parts of both the homogenizer and the mixer are electrically earthed.

In a preferred embodiment, as the mixture flows towards the reactor, it passes through an alternating mixing device to which initially the mixture passes through a vertical (up and down) mixing device and subsequently passes through a horizontal side to side mixing device. Irrespective of the technique that is used it is important that a homogenous mixture of ortho-xylene and oxygen-containing gas (air) is maintained from the injection zone to the reactor.

The ortho-xylene vapour and oxygen-containing gas mixture then enters a multi-tubular reactor filled with coated ceramic ring catalyst particles, for reaction at a temperature typically of from 350° C. and to 460° C. The inlet pressure at the reactor tubes may be in the range of 0.3 to 0.6 barg, typically about 0.45 barg, and the pressure drop across the tube may be in the range of 0.2-0.4 bar, typically about 0.3 bar. We prefer to use a catalyst giving a lower pressure drop across the tube, because this allows to reduce the discharge pressure, and consequently also the energy requirement, of the compressor feeding the oxygen-containing gas to the process, which is an important energy consumer. A further advantage of this reduced pressure drop is that the reactor inlet pressure may be reduced, which reduces the holdup of flammable material inside the equipment, affecting the size and number of rupture disks desired for safe operations, and also reduces the flammability range of the ortho-xylene and oxygen-containing gas mixture. When replacing a catalyst system having a higher pressure drop with a catalyst system having a lower pressure drop, we found it advantageous to also adapt the air or oxygen-containing gas compressor rotor, the gearbox and/or its driver to the new requirements, such that the new operating point remains in the highest efficiency operating envelope of the equipment, and the energy savings could be fully realised. The residence time within the catalyst tubes may be in the range of 0.5 to 2 seconds, typically about a second. The tubes are usually arranged vertically, with the reaction mixture of gas and ortho-xylene passing in a downward direction through the tubes.

The oxidation reactor typically is a tubular reactor comprising a plurality, preferably a multitude of tubes, packed with the oxidation catalyst to form catalyst beds. The catalyst beds in the reactor tubes preferably are preceded by a layer of inert rings preferably uncoated ceramic rings with a thickness of 5-20 cm, which typically is provided on top of the catalyst. The layer of inert rings can be heated from the outside of the reactor tube, and the rings preferably are made of material having high thermal conductivity, to enhance the further heat up of the gas ortho-xylene mixture as it enters the tubes, by thermal conduction from the wall of the reactor vessel. A thicker inert layer is less preferred, as it will be at the expense of effective conversion capacity. The inert layer can also provide further protection against non-vaporised ortho-xylene droplets and can enable additional mixing of the ortho-xylene/gas mixture. Preference is given to only pack inert material into the upper section of the reactor tubes, at the height of the tubesheet, as it is difficult to remove heat of reaction if a catalyst were to be present in that location.

The preferred catalyst is a multi-layer catalyst system composed of a mixture of vanadium pentoxide, titanium dioxide, and several other metal, alkali and earth-alkali components in varying concentrations, typically coated on a ceramic ring or hollow cylinder material. Such a hollow cylinder may e.g. have 7 mm as the outer diameter (OD) and 4 mm as the inner diameter (ID), and have a height (H) of 7 mm. Alternatively the cylinder may have 8×6×5 mm as (OD×H×ID) dimensions. The catalyst layers preferably have increasing activity along the tube in the direction of flow of the ortho-xylene, oxygen-containing gas mixture. Catalysts which can be used are described, for example, in DE 25 10 994, DE 25 47 624, DE 29 14 683, DE 25 46 267, DE 40 13 051, WO 98/37965 and WO 98/37967. Coated catalysts in which the catalytically active composition is applied in the form of a shell or coating to the support, such as for example in DE 16 42 938 A, DE 17 69 998 and WO 98/37967, have been found to be particularly useful. The catalyst may be pre-calcined or may be calcined in-situ in the oxidation reactor, although it is preferred that a pre-calcined catalyst is used, as the use of an in-situ calcined catalyst is much more sensitive for developing a runaway reaction than a pre-calcined catalyst. A runaway reaction is the result of a rapid increase of the ortho-xylene concentration, for instance from an inhomogeneous ortho-xylene/gas mixture. The runaway reaction leads to the formation of a localized hot spot development inside the catalyst tube, which can ignite the reaction mixture and also the upstream ortho-xylene/gas mixture by backfiring. In such event, the flame moves counter currently against the gas flow direction, and at a velocity that is higher than the gas velocity.

The tubes in the reactor are preferably thin walled tubes, preferably made from mild carbon steel, and are typically of internal diameter from 20 to 30 millimeters, preferably from 23 to 27 millimeters. It is preferred that the tubes are longer than 2.5 meters and a length of 3.25 to 4 meters is preferred, more preferably 3.4 to 3.8 meters. It has been found that use of tubes of this length allows more catalyst to be available to the mixture of ortho-xylene and the oxygen-containing gas, allowing a lower temperature to be used, whilst retaining the conversion which is virtually 100%. The use of the lower temperature results in a higher reaction selectivity to ortho-xylene, which is typically in the range 80 to 85%. The reaction is highly exothermic and the temperature of the reaction is controlled by providing a coolant flowing around the outside of the tubes within the reactor, on the reactor shell side. The preferred coolant is molten salt, generally maintained at a temperature in the range of from 320° C. to 380° C. The coolant temperature may be increased over the length of a commercial run to compensate for any deactivation of the catalyst.

The reactor product is a gas which leaves the reactor typically at about the cooling salt temperature of for example 320-380° C. and typically first enters a gas cooler where it is first cooled, for example to about 175° C. at which temperature the product is still a vapour. In the next phase of the cooling stage, the gas is optionally cooled further in a liquid condenser, preferably to about 138-142° C. Part of the crude phthalic anhydride is condensed in the liquid condenser and preferably also separated off, whereas the remaining gaseous material flows to one or more switch condensers. The cooling is typically performed against raising steam from condensate on the utilities side of the cooler and the liquid condenser. We have found that in order to avoid local condensation, and consequently fouling, in the gas cooler, it is preferable to feed a condensate for steam generation that is already at a temperature of at least 135° C., more preferably at least 150° C., if needed by a preheater on this condensate stream. If the phthalic anhydride facility is in the proximity of a phthalate ester production facility, the condensate from the steam used for heating the phthalate ester facility may readily be used for generating the steam in the phthalic anhydride facility, optionally after flashing the condensate to a lower pressure level. The low pressure steam vent from this flashing may also be recovered by condensation to further condensate. The steam generated by the phthalic anhydride facility may be integrated with a steam system supplying other heat consumers.

In a switch condenser, the gaseous phthalic anhydride is desublimated, typically in the form of needles, on a cold surface, a process step that is typically followed by a melting stage. The cooling for the desublimation is preferably performed at about 60° C., typically using a heat transfer oil as the coolant, whereas the melting is performed at about 180° C., typically also with the same type of oil. The switching of the equipment from desublimation to melting and back causes thermal stress and fatigue, in particular on the welds, and we have found that the switch condenser life time may be extended by limiting the temperature change rate of the heat transfer oil to at most 50° C. per minute, and preferably also by limiting the maximum heat transfer oil temperature to at most 180° C.

We have also found that acoustic emission monitoring may be a suitable tool to monitor the development of microfractures in the steel of the switch condensers, more particularly in the welds therein, and to provide an indication of when these microfractures may be growing or condensing and eventually lead up to a size where a leak is likely to occur. When a leak occurs, hot oil typically leaks into the product phthalic anhydride and contaminates the product to a typically unacceptable degree, such that the leaking switch condenser must be taken out of service and repaired. We have found that acoustic emission monitoring of the switch condensers may help in forecasting failure risk, in the planning of further inspections and maintenance interventions, thereby introducing a preventive element into the switch condenser maintenance which otherwise would be more strictly remediating.

The products from the liquid condenser and the switch condensers are preferably combined as crude phthalic anhydride, which flows to the intermediate tank for feeding to distillation. The condenser system also purifies the product, the liquid condenser typically reaching 95-98% purity while the switch condensers usually give an even higher purity.

The waste gas of the switch condensers typically has a temperature of 65° C. to 75° C. and can conveniently be disposed off in a catalytic incinerator. The remaining organics in the waste gas may be combusted at for example 290-350° C. over a multi-layer honeycomb catalyst. The off-gas of the incinerator is then preferably discharged to the atmosphere. Alternatively, the waste gas of the switch condenser can be disposed of into a thermal incinerator or passed to an aqueous scrubber system to recover some of the organic materials from the waste gas, such as maleic anhydride.

After the condensation section, the condensed and desublimated liquid phthalic anhydride passes to a final purification step, comprising a thermal treatment step followed by distillation, typically in one to three stages. The thermal treatment dehydrates any phthalic acid that may have been formed during the oxidation reaction, or downstream thereof in the presence of even traces of water, and is followed by or combined with a treatment with a base, which can neutralise any acid species, including remaining traces of phthalic acid, that may be present. The purification may be performed separately on the products from the liquid condensers and the switch condensers, or the materials may be combined prior to purification. The dehydration is typically performed by heating, typically to a temperature in the range 250° C. to 290° C., and the neutralisation may be performed with a base such as potassium hydroxide or sodium carbonate.

Sodium hydroxide may also be used, but is less preferred because of the risk of stress corrosion of construction materials. These steps may be performed concurrently in a single vessel or sequentially in two vessels. We prefer however to first heat treat, to dehydrate any phthalic acid present, and then to treat with the base to neutralise, as this optimises the yield of phthalic anhydride and avoids the base converting phthalic acid to the undesirable impurity benzoic acid. We also prefer that the neutralisation be performed with potassium hydroxide.

Finally, after the thermal treatment stage, the pure phthalic anhydride can pass to a stabiliser section to remove light components like benzoic acid, followed by a product distillation section to separate the phthalic anhydride product from heavier boiling byproducts, which two sections can be combined in a single section, optionally followed by a heavy by-product concentration section. The phthalic anhydride may then be provided as an intermediate for subsequent reactions either as a melt or as flakes.

Temperature control of the feed mixture and the oxidation reactor are extremely important, and heat input provisions, such as electrical tracing and/or steam tracing and/or steam jacketing, and insulation according to this invention are preferably employed to prevent condensation of ortho-xylene and reaction products on cold spots, particularly at the nozzles connecting various sections of the process equipment and the rupture discs. The insulation is preferably sealed to prevent water entering the insulation, which may impair its performance or damage its integrity. When steam tracing or jacketing is used, it is our preference to provide steam at a pressure of at least 8 barg, even better 12 barg, preferably at least 15 barg, more preferably at least 16 barg and most preferably at least 19 or even 20 barg to the means providing heat to the equipment nozzles, particularly importantly those connecting the rupture discs which relieve the reactor contents to the atmosphere upon a deflagration. A further preference is to put an insulating mineral wool blanket on top of the rupture disc surface, with a foam cap preferably of polyurethane being provided on top of the rupture disc relief stack to prevent rain and cold air coming into contact with the rupture disc surface, so preventing cool down of the process. The foam cap protects against ingress of water, hail or snow into the relief stack and collecting on top of the rupture disc, and creating possible cold spots on the rupture disc. The cap is preferably lightweight and disintegrates easily upon blowing the disc and the resulting foam fragments are dispersed without being a danger to people who may be present. The preferably 3-8 cm thick insulation blanket is laid down carefully onto the disc so as not to hamper the relieving performance of the rupture disc.

At start-up, it is preferred to operate at a low loading below the explosive region for an initial period. For example, the facility may operate for 6-24 hrs at 42 g ortho-xylene loading (below the explosive region) to "burn out" any pyrophoric compounds that may be present inside the process equipment. Pyrophoric compounds may for instance be formed from the reaction products resulting from the corrosive action by acids such as maleic acid and phthalic acid. These include iron maleate, iron phthalate, nickel maleate, nickel phthalate, chromium maleate, chromium phthalate and other organic salts of metal present in the steel of the facility where this is in contact with the ortho-xylene feed and/or with reaction products.

It is important to maintain low levels of impurities in the ortho-xylene feed. Impurities that may occur in the ortho-xylene feed include cumene or isopropyl benzene, styrene, ethyl benzene and methyl ethyl benzene. It is particularly important for operations at high loading that the cumene level is limited to below 0.3 wt % based on ortho-xylene, because we have found that at higher cumene levels, in combination with ortho-xylene loadings at and above 85 g/Nm$^3$, the likelihood of having a deflagration increases significantly. Peroxides may come from the ortho-xylene. For instance, cumene and oxygen can make hydroperoxide, and this may already occur in the feed tank if that is not blanketed with an inert atmosphere. It may also occur in a truck or a ship during transport of the ortho-xylene. This hydroperoxide is unstable under vaporising conditions, and can cause a chain reaction forming more cumene peroxide and ortho-xylene hydroperoxide, potentially leading to deflagrations. Styrene, ethyl benzene and methyl-ethyl benzene are other possible sources of peroxides which may develop in the ortho-xylene storage tank or during shipment. We have found that concentrations of styrene exceeding 500 ppm may cause polymerisation and lay down of the resulting polymer on the spray nozzle assembly, which due to the insulating properties of the polymer eventually leads to build up of static charge, which may result in a deflagration. Furthermore, ortho-xylene and oxygen in the gas may react to form some ortho-xylene hydroperoxide as an intermediate in the formation of the aldehyde. General fouling may also provide a surface for peroxide formation, and this can occur with improper air filtration, and/or in a dusty environment. Accumulation of peroxide in a layer of fouling is known to initiate deflagrations.

The present invention therefore provides an improved process and apparatus for providing and maintaining a mixture of the hot oxygen-containing gas and the hot ortho-xylene and for the production of phthalic anhydride which enables operation at high loading, whilst minimising the risk of explosion and/or deflagration while operating within the explosive temperature range.

The present invention is illustrated by reference for the accompanying drawings in which FIG. 1 shows curves illustrating the dew point of ortho-xylene at a particular pressure and concentration in air.

Figure 1:
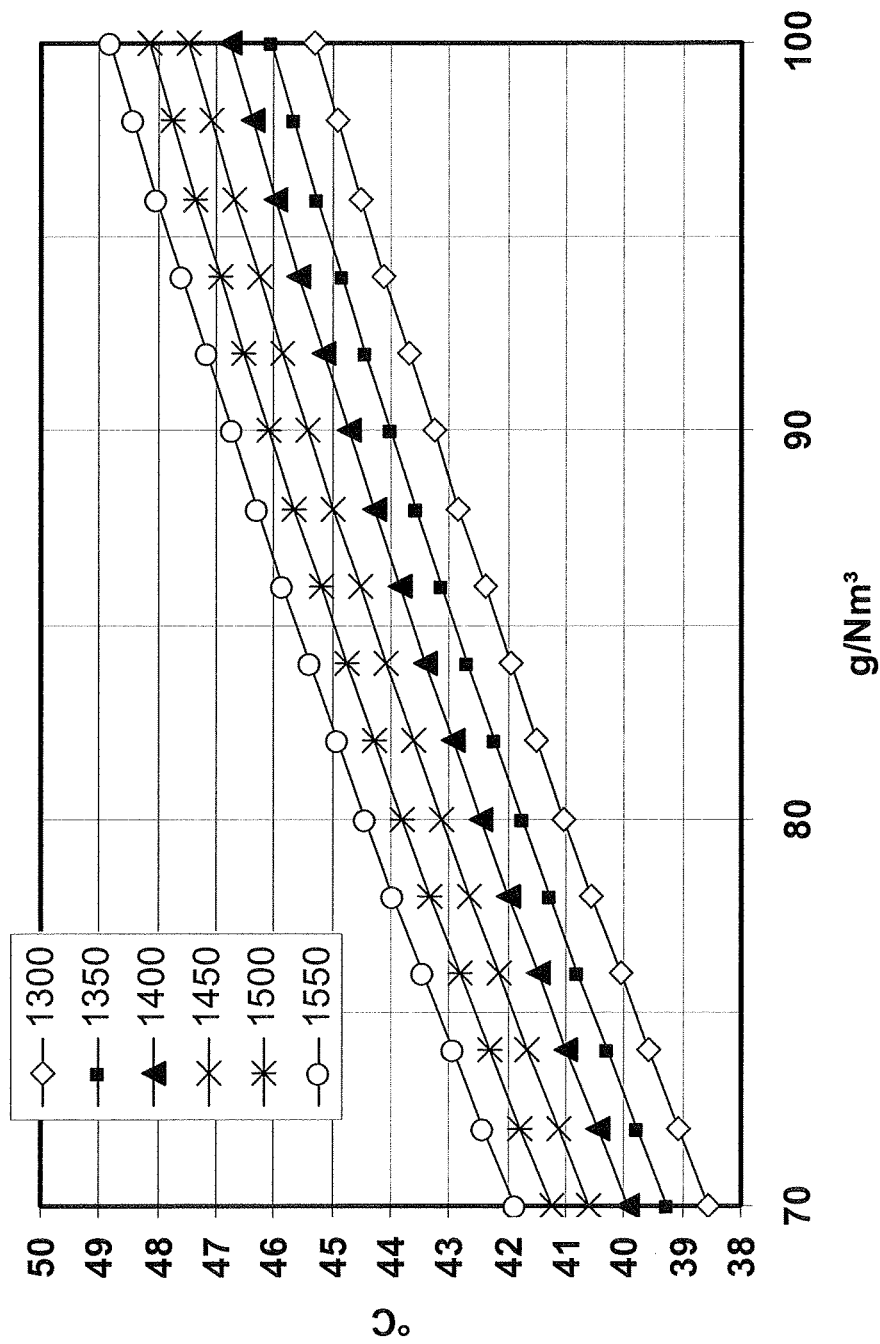

FIG. 1 shows curves of how the dew point of ortho-xylene changes with the concentration of the ortho-xylene and with absolute pressure of a mixture of ortho-xylene vapour and air as the oxygen-containing gas. The concentration of ortho-xylene is for convenience expressed as ortho-xylene loading, expressed as grams per Nm$^3$ of air. The curves are for absolute pressures ranging from 1300 mbar as the lowest curve, and 1550 mbar for the highest curve shown. These curves may be helpful for quickly determining the dew point of the ortho-xylene in the mixture depending on loading and pressure, without having to do the actual calculations.

Figure 2:
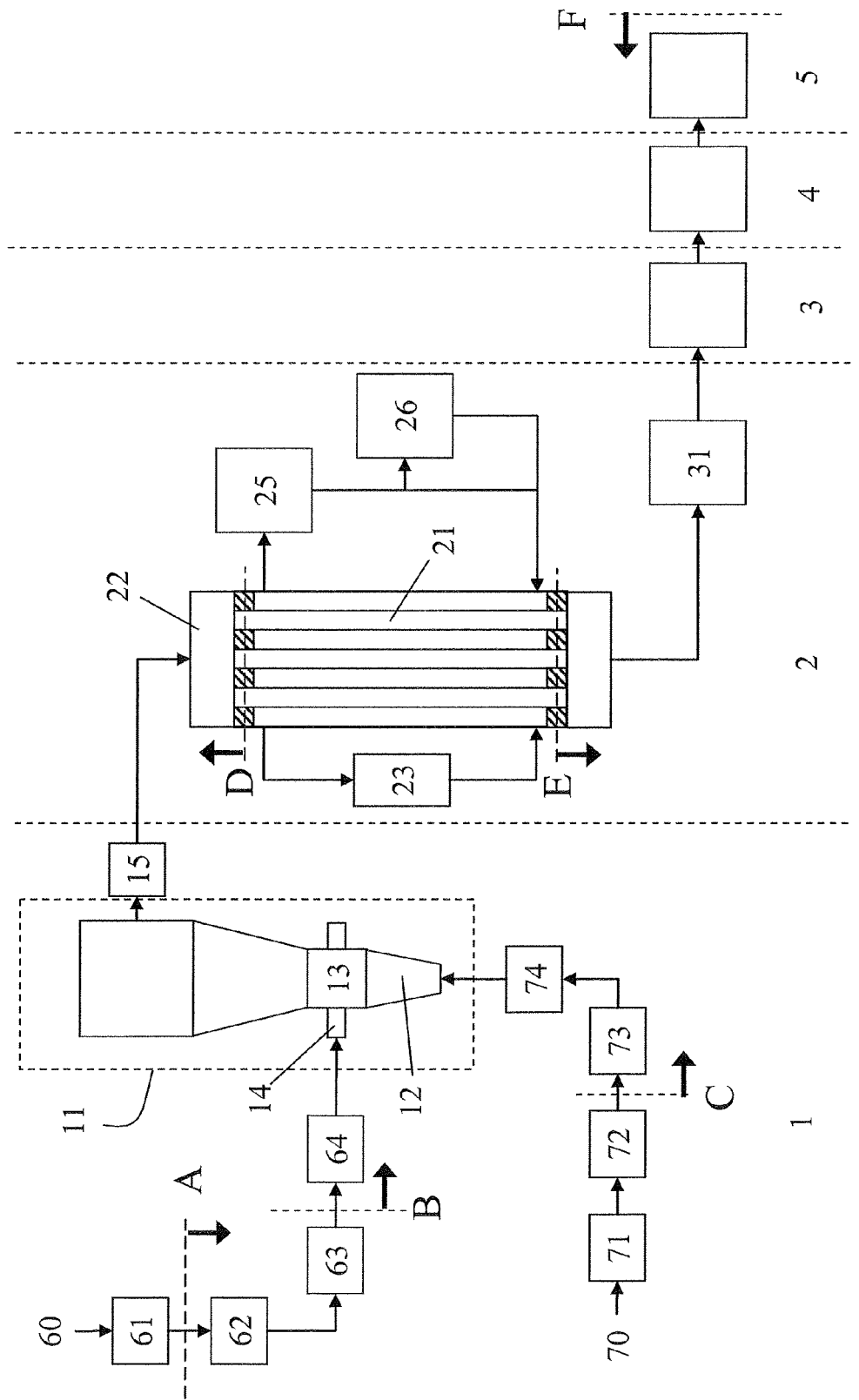
FIG. 2 shows the overall layout of the oxidation section of a phthalic anhydride manufacturing facility, as well as the parts of the equipment that preferably are thermally insulated and/or electrically grounded to earth and/or electrically interconnected.

FIG. 2 is a schematic illustration of the oxidation section of a plant for the manufacture of phthalic anhydride from a mixture of air and ortho-xylene.

The oxidation section consists in general of the following sub-sections, the raw material section (1); the reaction section (2); the post-reactor section (3); the partial liquid condenser section (4) and the switch condenser section (5).

In the raw material section (1) air is taken from the environment (70), through a filter (71) by a blower (72), and fed to a preheater (73) after which it may be passed through a first turbulence reducer or "straightening vanes" (not shown) and its flow is measured accurately in a flow meter (74). The flow meter preferably is a venturi flow meter, with corrections for pressure and temperature to increase accuracy. The heated air is then fed through a lower sieve basket provided with a turbulence quietening vane system (see FIG. 3) to the mixing zone (13) of the evaporator section (11) where it is mixed with a mist of heated ortho-xylene provided from the ring feed system (14); the lances for the introduction of the ortho-xylene are not shown in FIG. 2. The ortho-xylene feed is taken from its supply point (60) by a pump (61) through a filter (62) to an accurate flow metering and control system (63), preferably comprising a mass flow meter, after which it is preheated in a preheater (64) before it is fed as a liquid to the ring feed system (14) of the evaporator section (11) for spraying it as a mist into the flow of heated air going through the mixing zone (13). The mixture of ortho-xylene and air then passes through an upper sieve basket (not shown in FIG. 2) into a further two-stage mixing zone (15) of the evaporator where the mixture is homogenised. The mixture first passes through a perforated screen and then a static mixing device. A preferred mixing device is a Sulzer SMV static mixer with two mixing elements in which the ortho-xylene/air mixture in the first element is mixed in the vertical upward and downward direction, followed by mixing in the second element in the horizontal directions.

The mixture then passes to the reaction sub-section (2). The reaction sub-section consists of a reactor (22) containing a series of vertical tubes (21) packed with catalyst (not shown). The internal temperature of the reactor and the temperature of the reaction tubes (21) are controlled by molten salt circulating on the reactor shell side, and which is provided from a salt pump (25). A major part of the salt flows to the reaction tubes for cooling. Part of the salt is passed to a salt bath cooler (26) in which the salt exchanges heat with hot water to generate steam. The returning cooled salt is mixed with the returning salt from the reactor before entering the salt pump. A minor part of the salt is passed to a steam superheater (23).

On exiting the reactor, the phthalic anhydride vapour is cooled in the gas cooler (31) and passes to the optional post-reactor section (3), which may comprise an extra catalyst bed, preferably adiabatic, typically of even more active catalyst as compared to the catalysts used in the tubular reactor. Next the cooled gas passes to the optional liquid condenser section (4) where the crude phthalic anhydride is partially condensed, the remaining vapour passing to the switch condenser section (15).

It is our preference that the thermal insulation starts on the ortho-xylene and the oxygen-containing gas delivery sections at the inlet of the preheaters (64 and 73), indicated with points B and C respectively in FIG. 2. We prefer this thermal insulation to continue up to the top tubesheet of the tubular reactor (22), indicated with point D in FIG. 2. Further thermal insulation is preferably also provided from the bottom tubesheet of the tubular reactor (22), indicated with point E in FIG. 2, continuing downstream up to and including the switch condensers (5), indicated with point F in FIG. 2. We have found that cold spots downstream of the catalyst bed are to be avoided because they may lead to pyrophoric material building up and also leading to deflagrations.

Electrical grounding and interconnections of adjacent metal parts of the equipment in contact with the process streams preferably starts on the ortho-xylene supply system from the inlet of the filter(s) (62), indicated with point A in FIG. 2, and from point C on the oxygen-containing gas supply system down to point D as defined above.

Figure 3:
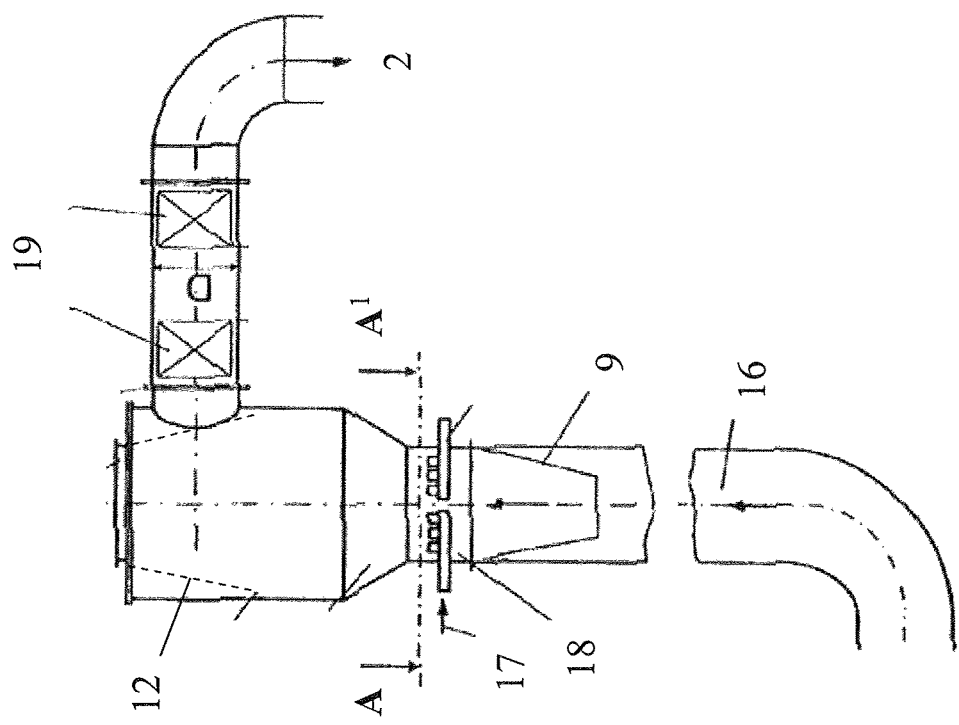
FIG. 3 is a section through the evaporation section of the facility shown in FIG. 1.

FIG. 3 is a schematic cross-sectional illustration of the apparatus in the evaporator sub-section of the oxidation section as illustrated in FIG. 2. FIG. 3 shows the air stream (16) passing upwards through a lower sieve basket and the quietening vane system (9) and then shows the hot ortho-xylene (17) being injected into the heated air stream through the spray nozzles (18). The ortho-xylene is vaporised in the heated air and the hot vapour mixture passes side-wards through an upper sieve basket (12), which is a perforated screen, and a vapour homogeniser such as a static mixing device (19) before passing to the reaction sub-section (2).

Figure 4:
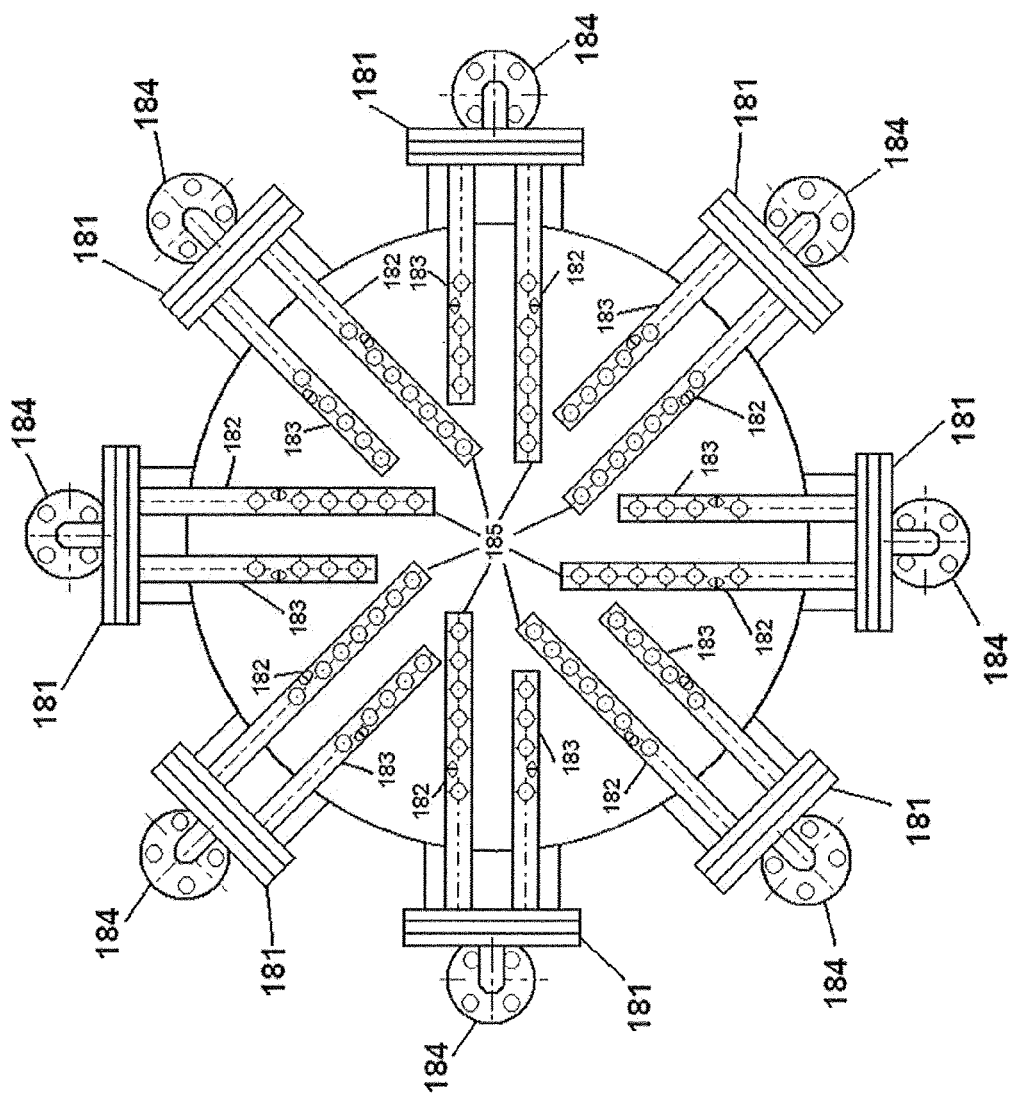
FIG. 4 shows the location of the lances carrying spray nozzles of the present invention within the evaporator section shown in FIG. 3.

FIG. 4 is a cross section through A-A$^1$ of FIG. 3 looking downwards onto a spray nozzle system (18) that may be employed according to the present invention.

FIG. 4 shows eight lances (181) projecting through the wall of the evaporator, each lance being provided with two limbs, a longer limb (182) and a shorter limb (183). Each lance (181) is also provided with means (184) for connection to the supply of heated ortho-xylene. The limbs of the lances are provided with nozzles for the spray of the ortho-xylene into the stream of hot air, shown in one of the possible nozzle arrangements. In the embodiment illustrated in FIG. 4 the longer limb of each lance is provided with 7 nozzles and the shorter limb is provided with 5 nozzles, although the number of nozzles can be varied. The connection of the lances to the ortho-xylene supply system is by a ring system (not shown) common to all the lances and the whole introduction system is thermally insulated to prevent cooldown of the ortho-xylene feed.

The phthalic anhydride produced according to the invention may be used for esterification with an alcohol or an alcohol mixture to produce the corresponding di-ester. Suitable esterification processes are disclosed in WO 2005/021482, WO 2006/012989 and in pending patent applications U.S. Ser. No. 60/906,732 and U.S. Ser. No. 60/906,797. The alcohol may be a secondary alcohol, such as isopropanol, but is preferably a primary alcohol. Suitable primary alcohols are $C_1$-$C_{13}$ primary alcohols, and may be branched or unbranched, such as methanol, ethanol, n-propanol, n-butanol, isobutanol, isohexanol, isoheptanol, iso-octanol, 2-ethyl-hexanol, isononyl alcohol, 2,4-dimethyl heptanol, normal decanol, isodecanol, isoundecyl alcohol, 2-propyl heptanol, undecyl-dodecyl alcohol, isotridecyl alcohol and mixtures thereof. Dimethylphthalate and diethylphthalate are preferred products for personal care applications. The phthalates with alkyl chains having 4 or more carbon atoms, up to 13, are used as plasticizers for polyvinyl chloride (PVC). The process of the invention is suitable for producing all these phthalates, in particular those produced from alcohols or alcohol mixtures having an average of 8 to 10 carbon atoms, especially those having an average of approximately 9 carbon atoms, such as those designated as DOP, DINP, DIDP and DTDP. Di-isononyl phthalate (DINP) is highly preferred as a PVC plasticiser, and so is di-isodecyl phthalate (DIDP). Also suitable is di-propylheptyl phthalate (DPHP) These higher molecular weight phthalates provide a higher permanence in the flexible PVC end product compared to the lower molecular weight equivalents such as di-2-ethylhexyl phthalate (DEHP or also called DOP). Di-isotridecyl phthalate (DTDP) is preferred in low volatility applications such as special purpose wire and cable manufacture. These phthalate esters may further be hydrogenated to form their corresponding 1,2-cyclohexane dicarboxylic acid esters, such as e.g. di-isononyl dicyclohexanoate, as disclosed in WO 2003/029339 The latter hydrogenation step may be performed by techniques known in the art, such as by using the processes described in EP 1042273 or WO 2004/046078.

The alcohols used in the esterification may be so-called oxo-alcohols, produced by the hydroformylation of olefins, when necessary followed by hydrogenation of the aldehyde intermediate. Suitable processes for hydroformylation are disclosed in WO2005/058787 or in copending applications PCT/EP2008/053783 and PCT/EP2008/053718, and suitable processes for aldehyde hydrogenation are disclosed in WO2005/058782.

The hydroformylation and hydrogenation processes for producing the oxo-alcohols, as well as the process for hydrogenating the phthalate ester, need a source of hydrogen. The hydrogen may be supplied from a variety of sources, such as but not limited to refinery processes, partial oxidation (PDX) of various starting materials, steam reforming, autothermal reforming (ATR) or the like. One of the potential sources of hydrogen is a refinery process called catalytic reforming, sometimes also called a Platforming process, wherein a refinery liquid stream, typically a naphtha or equivalent containing primarily naphthenes and/or paraffins in the C6 to C11 range, is converted to a product rich in aromatics over a heterogeneous precious metal chloride catalyst. These kind of processes are often known as a "Powerformer" or "Powerforming" processes (developed by Exxon), or as Continuous Catalyst Regeneration (CCR) processes (as e.g. offered by UOP and IFP). The hydrogen from such a catalytic reforming processes contains small amounts of chloride, at a level in the order of 1-10 ppm by volume. It is believed that most of this chloride is present as hydrogen chloride, which is more readily detected by direct gas analysis and at a typical level of 4-8 ppmv. It is however suspected that, in addition, also organic chlorides may be present, and possibly even at similar levels as the HCl. Many hydrogen consuming processes are sensitive to chloride poisoning, and a chloride removal step is typically foreseen to remove HCl from the catalytic reforming hydrogen byproduct, most typically down to a level of at most 1 ppmv. A typical chloride removal step is the adsorption of chloride over activated alumina, such as alumina 9139A from UOP, C1-750 and C1-760 from BASF, Alcoa 760 from Alcoa, Puraspec from Johnson Matthey, over ZnO such as members of the Süd-Chemie Actisorb C1 series, e.g. C1 13, and/or over a molecular sieve, such as type CLR-454 obtainable from UOP or Unimol types from Unicat.

Some of the typical process steps in the production of the oxygenates, such as the alcohols, disclosed herein, may however be particularly sensitive to chloride poisoning, such as a copper chromite hydrogenation catalyst used for aldehyde hydrogenation. The alcohol production process may also employ a hydroformylation catalyst cycle comprising a closed loop with minimal purge, in particular an aqueous closed loop, such as with several of the techniques discussed herein and/or disclosed in U.S. Pat. Nos. 8,541,627 and 8,476, 476. Organic chlorides may become again converted to HCl in these processes. The traces of chloride coming with the hydrogen from a source such as a catalytic reforming may therefore build up in any of these aqueous loops to levels where corrosion due to chloride may become problematic, and/or where the chloride acts as a poison to the chemistry of the hydroformylation catalyst cycle, such as in a preforming step. The hydrogen from the catalytic reforming unit as feed to the alcohol production process therefore may need to be cleaned up to a lower level of chloride than for other hydrogen consuming processes, preferably to a level of at most 0.1 ppmv and more preferably at most 0.02 ppmv of chloride. We have found that the catalytic reforming hydrogen may also contain organic chloride compounds, at a concentration up to 10 ppm volume. Further we have found that organic chloride compounds are more difficult to remove by adsorption on the conventional adsorbents. Organic chlorides may therefore more easily pass through the adsorbent bed and still may cause problems in the alcohol production process. In addition, an activated alumina adsorbent may also convert part of the HCl in the hydrogen to organic chloride compounds. The activated alumina may react with HCl to form $AlCl_3$. This $AlCl_3$ is a catalyst for the formation of organic chlorides, and also for polymerizing trace olefins in the hydrogen stream to form heavier components, sometimes referred to as "green oil". Organic chlorides are more difficult to detect, and typically do not show on the conventional chloride analytical methods, such as the well known Dräger tube.

We have found that an alkali treated molecular sieve, more particularly an alkali treated zeolite, is less prone to producing organic chlorides and performs much better in such chloride removal service, also adsorbing organic chloride compounds, while capable of reaching chloride loadings of up to about 20-22% wt on the adsorbent, expressed on a dry and chloride-free basis. We prefer to use a chloride adsorbent based on an alkali-treated zeolite, more particularly a zeolite, having a pH of at least 10, preferably 11, when measured in slurry. The adsorbent may comprise other components such as magnesium aluminosilicate, and binder material, and may be in the form of spheres or extrudates. An example of a suitable alkaline zeolite is product NB 316 from CLS Industrial Purification, containing from 70-90% wt of zeolite and sodium oxide and from 10-30% magnesium aluminosilicate and having a body centre cubic crystal structure, a pH of 11, a nominal pore size of 10 Angstroms, and a surface area of 630 m2/g. The product is available as 1.6 mm diameter (1/16") spheres or as 1.6 mm (1/16"), 3.2 mm (1/8") or 4.8 mm (3/16") diameter cylinders. The zeolite of the adsorbent may be of mineral origin, or may be synthetic. The zeolite may have one single crystal structure, or be a mixture of zeolites with different crystal structures. We prefer to use a mixture of faujasite, having larger 12-ring pores, and Linde Zeolite A, which as smaller 8-ring pores. The adsorbent preferably comprises a binder material in addition to the zeolite, but could be binderless. Clay is a suitable binder material, such as chlorite. The adsorbent may be formulated from fresh zeolite, or may be based on a waste byproduct from a different process using a suitable zeolite as catalyst or adsorbent material, preferably after regeneration such as by oxidative regeneration. We prefer to use an adsorbent having a large surface area, of at least 300 $m^2/g$, preferably at least 400 $m^2/g$, more preferably at least 450 $m^2/g$, typically 488 $m^2/g$. Higher surface areas are also suitable, such as 500 $m^2/g$ or 600 $m^2/g$ and above. The activity and capacity of the adsorbent is preferably increased by treatment with an alkali solution, typically containing NaOH, $Ca(OH)_2$, KOH or a mixture thereof.

We prefer that only the hydrogen supply to the more sensitive consumers is treated with the alkali treated molecular sieve, so that the amount of generated spent adsorbent can be minimised. The catalytic reforming hydrogen going to the less sensitive consumers may preferably undergo only the conventional cleanup. When an activated alumina adsorbent is used for this conventional cleanup, we prefer to withdraw the hydrogen for treatment with the alkali treated molecular sieve upstream of the activated alumina adsorbent, so that the amount of organic chlorides in the hydrogen to be treated with the alkali treated molecular sieve is minimised. What is described here for hydrogen from catalytic reforming processes, is equally applicable to hydrogen from other sources that may contain chlorides for instance because of chloride being present in at least one their feedstocks.

Phthalic anhydride (PAN) has a melting point of about 131° C. and is solid at ambient temperature. It can therefore be converted from its molten form in the production process into solid flakes and stored, sold and handled commercially as flakes. In this case, it is not unusual that the PAN flakes are melted before the molten PAN is pumped into the consuming process. PAN is very often stored, sold, transported and handled in molten form, typically at temperatures of 160° C. or above.

The molten PAN exhibits a vapour pressure, and the vapour spaces in the equipment containing PAN therefore contain PAN vapours. Upon cooling of equipment items containing PAN vapours, the PAN may solidify as snow-like flakes. This may for instance occur in overhead systems, in vents of process equipment and/or storage vessels to the atmosphere, and in vapour clouds originating therefrom. The latter is undesirable from an environmental aspect, and may raise concerns of industrial hygiene because of possible effects of PAN on humans via contact with skin or by inhalation. Inside the equipment, it gives rise to concerns for plugging of equipment lines, possibly leading to vacuum pulling on storage tanks which may lead to tank collapsing.

We have found that these concerns can be significantly reduced by providing, at appropriate locations in overhead systems and vent lines, a solids knock-out volume wherein the vapour velocity is suddenly dropped for a short period. The effect is that a portion, if not all, of the flakes in the vapour stream are not carried further at the lower vapour velocities and collect at the bottom of the knock-out volume. The collected solids may then be recovered from the knock-out volume bottom at an appropriate time and be reintroduced into the process. In atmospheric vent lines, for instance, the knock-out volume may be provided by a "snow box", i.e. a wider piece of elbow or T-shaped pipe at the bottom of the vent stack, equipped with a manually removable cover on the side of the bottom volume or on one of the T-ends, through which the flakes can be removed t regular intervals.

We have found that these "snow boxes" and solids knock-out volumes are an interesting provision in the PAN production facility, as well as in the handling, storage and transportation facilities for PAN as a hot liquid, and also in the PAN consumption process facilities, such as a phthalate ester production plant.

We have found that the better locations to provide such solids knock-out volumes are the locations in the equipment where the vapours are cooler, typically also where the lower pressures occur. At these locations, the amount of solids that are formed and may be recovered is typically higher.

Having now fully described this invention, it will be appreciated by those skilled in the art that the invention can be performed within a wide range of parameters within what is claimed, without departing from the spirit and scope of the invention.

The invention claimed is:

1. An apparatus for the production of phthalic anhydride which comprises a reaction section comprising a fixed bed tubular catalytic reactor comprising an inlet tubesheet, and a raw material preparation section comprising
    (i) separate raw material delivery sections for a liquid and for a gaseous raw material,
    (ii) a raw material mixing section comprising a system for spraying the liquid raw material into the gaseous raw material to form a mixture of vaporised liquid and gas, and
    (iii) a mixture delivery section for delivering the mixture of vaporised liquid and gas to the fixed bed catalytic reactor,
    said apparatus further comprising
    at least one rupture disk on the raw material preparation section and/or on the reaction section, and
    wherein the raw material delivery sections each comprise a raw material heater, and
    wherein the apparatus further comprises equipment nozzles in fluid communication with process equipment, and wherein the external surfaces of the equipment nozzles, which are provided for connecting the individual elements of the process equipment in the raw material preparation section and/or in the reaction section up to the inlet tubesheet of the tubular reactor, and which are in contact with the mixture of vaporised liquid and gas, are thermally insulated.

2. The apparatus according to claim 1 wherein an insulating blanket is provided on the external surface of the rupture disc.

3. The apparatus according to claim 2 wherein the rupture disc is provided with a relief stack comprising a foam cap.

4. The apparatus according to claim 1 further comprising means for heating the thermal insulation.

5. The apparatus according to claim 4 wherein the heating means is electrical tracing and/or steam tracing and/or steam jacketing.

6. The apparatus according to claim 1 further comprising means for direct or indirect electrical grounding of metal parts of piping, instrumentation and process equipment of the apparatus that in use are in contact with the liquid and/or vaporised liquid raw material and/or the oxygen-containing gas and/or the mixture of vaporised liquid and gas.

7. The apparatus according to claim 1 comprising at least one set of two flanges for connecting equipment components and/or piping and/or instrumentation that in use are in contact with the liquid and/or vaporised liquid raw material and/or the oxygen-containing gas and/or the mixture of vaporised liquid and gas, and wherein at least one metal cable is electrically connected to both of the flanges of the connecting flange set.

8. The apparatus according to claim 1 comprising at least one lance projecting into the raw material mixing section, said lance comprising at least one spray nozzle for spraying the liquid raw material into the gaseous raw material to form the mixture of vaporised liquid and gas in the raw material mixing section.

* * * * *